United States Patent [19]
Euteneuer et al.

[11] Patent Number: 4,943,278
[45] Date of Patent: Jul. 24, 1990

[54] DILATATION BALLOON CATHETER

[75] Inventors: Charles L. Euteneuer, St. Michael; Richard C. Mattison, Mound; Daniel O. Adams, Blaine; Thomas R. Hektner, Minnetonka; Peter T. Keith, Edina, all of Minn.

[73] Assignee: SciMed Life Systems, Inc., Maple Grove, Minn.

[21] Appl. No.: 162,004

[22] Filed: Feb. 29, 1988

[51] Int. Cl.$^5$ ............................................. A61M 29/00
[52] U.S. Cl. ........................................ 604/96; 606/194
[58] Field of Search ................. 128/344, 348.1, 325; 604/96, 97, 102, 122; 606/191, 194

[56] References Cited

U.S. PATENT DOCUMENTS

| | | |
|---|---|---|
| 4,137,906 | 2/1979 | Akiyama et al. |
| 4,261,339 | 4/1981 | Hanson et al. |
| 4,327,709 | 5/1982 | Hanson et al. .................. 604/96 |
| 4,561,439 | 12/1985 | Bishop et al. |
| 4,597,755 | 7/1986 | Samson et al. .................. 604/96 |
| 4,638,805 | 1/1987 | Powell ................................ 128/344 |
| 4,771,776 | 9/1988 | Powell et al. ..................... 128/344 |
| 4,771,778 | 9/1988 | Mar ..................................... 128/344 |
| 4,790,315 | 12/1988 | Mueller et al. ................... 128/344 |
| 4,821,722 | 4/1989 | Miller et al. ..................... 128/344 |

FOREIGN PATENT DOCUMENTS

| | | | |
|---|---|---|---|
| 8606285 | 11/1986 | World Int. Prop. O. | 128/344 |
| 8800844 | 2/1988 | World Int. Prop. O. | 128/344 |

Primary Examiner—John D. Yasko
Assistant Examiner—Denise W. DeFranco
Attorney, Agent, or Firm—Kinney & Lange

[57] ABSTRACT

A balloon catheter for use in angioplasty includes an elongated flexible thin walled metal tube which carries an inflatable balloon at its distal end. A core member of smaller outer diameter than the metal tube is attached to the distal end of the tube to provide support for and guiding of the balloon section.

31 Claims, 2 Drawing Sheets

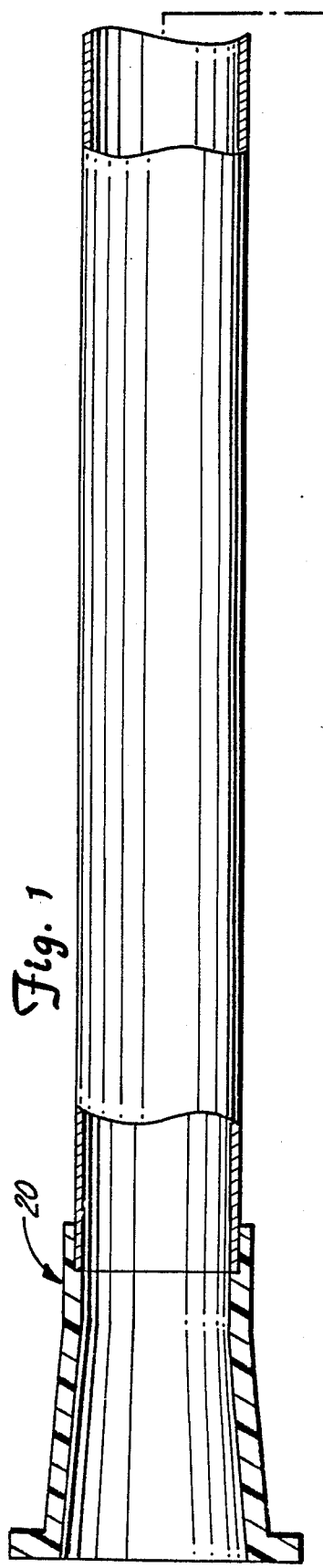
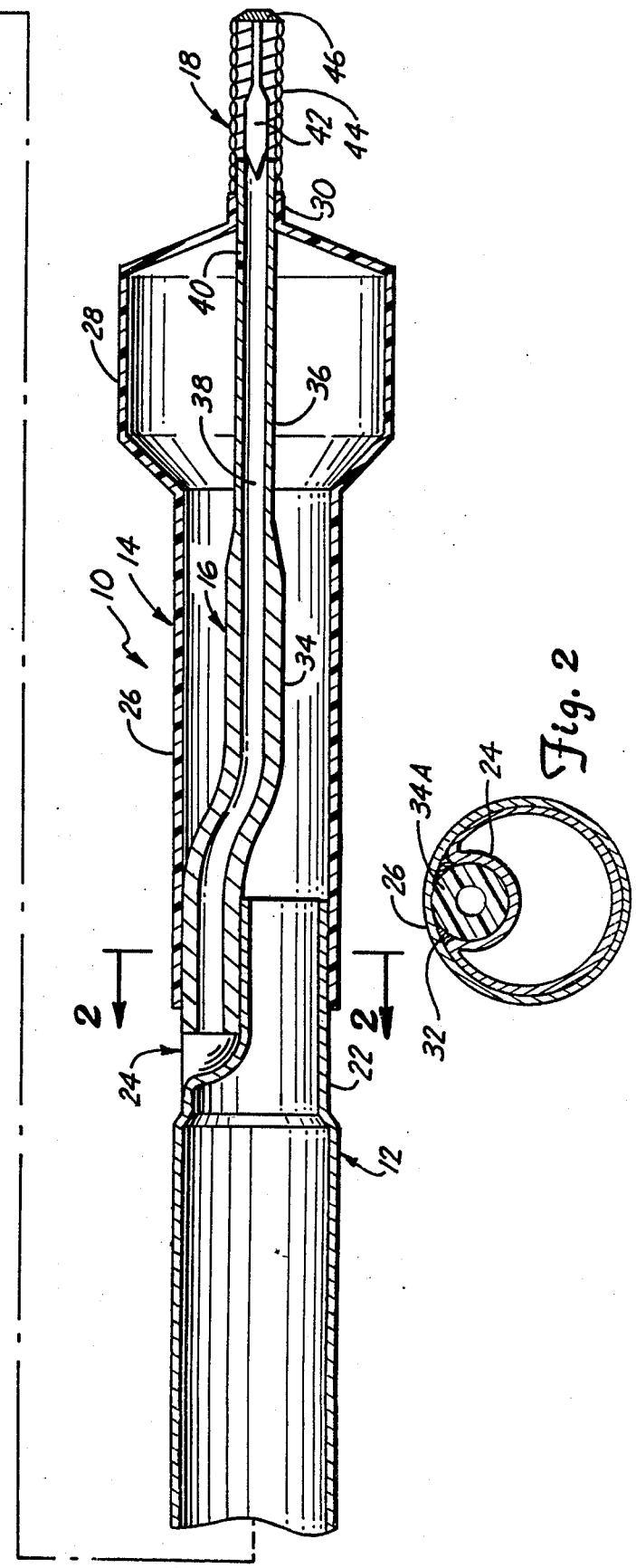

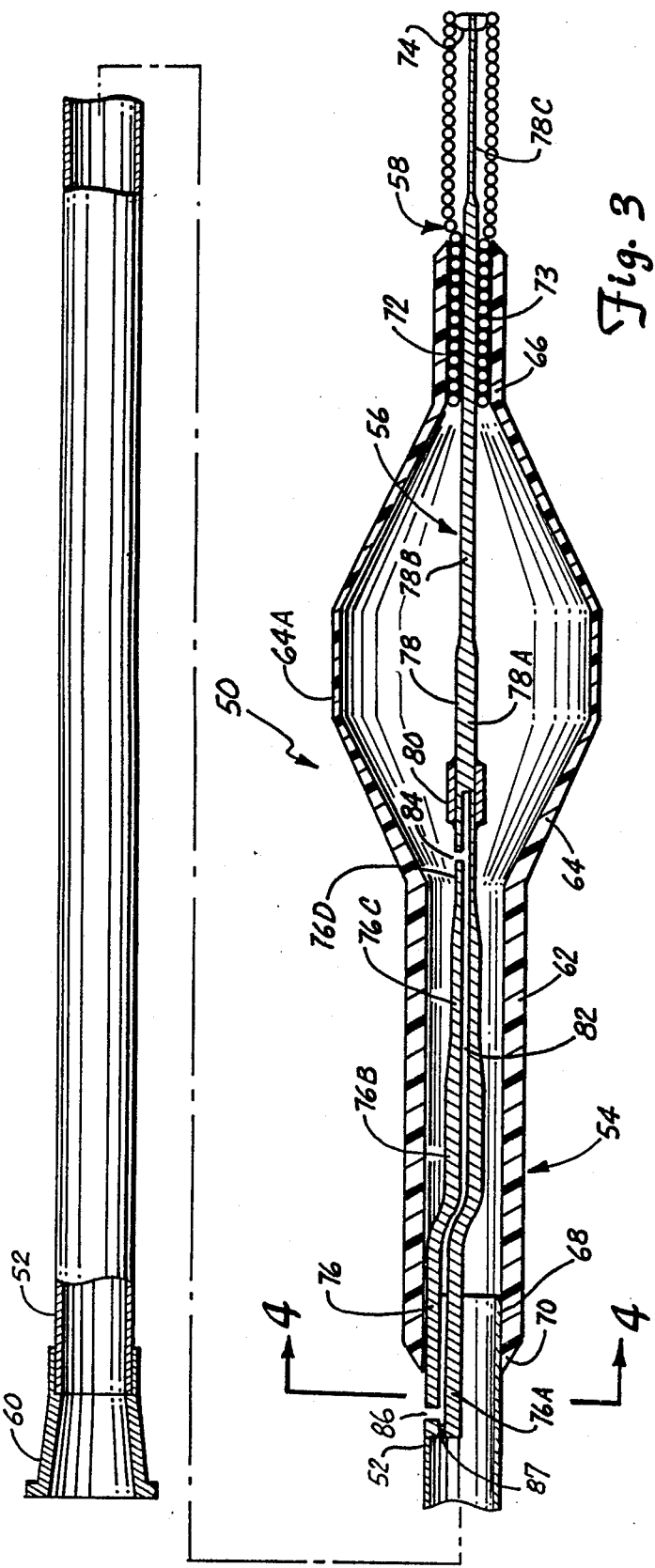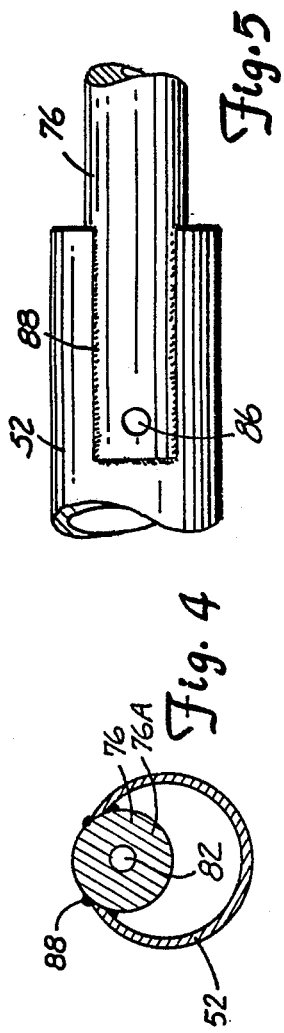

DILATATION BALLOON CATHETER

BACKGROUND OF THE INVENTION

1. Field of the Invention.

The present invention relates to the field of angioplasty. In particular, the present invention relates to a dilatation balloon catheter.

2. Description of the Prior Art.

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying fluid under pressure through an inflation lumen to the balloon. The inflation of the balloon causes stretching of the artery and pressing of the lesion into the artery wall to re-establish acceptable blood flow through the artery.

In order to treat very tight stenoses with small openings, there has been a continuing effort to reduce the profile of the catheter so that the catheter cannot only reach but also cross such a very tight stenosis.

In addition, a percutaneous transluminal coronary angioplasty (PTCA) system has been developed by applicant's assignee which makes use of a very low profile balloon catheter or "dilating guide wire" over which a second dilatation catheter can pass. The smaller dialating guide wire is first moved across a very tight stenosis, and the balloon of the dilating guide wire is inflated to partially open the stenosis. Subsequently, the larger diameter dilatation cathether is advanced over the dilating guide wire and across the stenosis. The balloon of the larger diameter catheter is then inflated to open further the stenosis.

The need to decrease dilatation catheter profiles has, however, brought with it certain practical limitations. In particular, the ability to transmit torque from the proximal to the distal end of the guide wire (or the catheter) in order to steer its distal tip through the vascular system and across a stenosis has been compromised. The need to reduce profile can compromise purgeability using conventional vacuum techniques. Therefore, there is a continuing need for improved torque response and tip control along with continued efforts for reduction in catheter profile, while facilitating a positive pressure purge.

SUMMARY OF THE INVENTION

The catheter of the present invention includes a hollow elongated flexible metal tubular member which has an inflatable balloon member mounted at its distal end. Also connected at the distal end of the metal tubular member is a core member (wire or tube) which extends through the balloon member. A first end of the balloon member is connected to the distal end of the metal tubular member, and a second end of the balloon member is attached to the core member. The interior of the balloon is in fluid communication with an interior passage of the metal tubular member. Inflation and deflation of the balloon is provided through the interior passage of the metal tubular member.

In preferred embodiments of the present invention, the core member has a vent opening which communicates with the interior of the balloon member. This allows air to be purged from the balloon through the vent opening and out through a passage in the core.

BRIEF DESCRIPTION OF THE DRAWINGS

FIG. 1 is a sectional view of a first preferred embodiment of the balloon catheter of the present invention.

FIG. 2 is a sectional view along section 2—2 of FIG. 1.

FIG. 3 is a sectional view of a second preferred embodiment of the balloon catheter of the present invention.

FIG. 4 is a sectional view along section 4—4 of FIG. 3.

FIG. 5 is a detail view showing a brazed bond between the tube and core shown in FIG. 4.

DETAILED DESCRIPTION OF THE PREFERRED EMBODIMENTS

Catheter 10 shown in FIGS. 1 and 2 is a dilatation balloon catheter which includes main catheter tube or shaft 12, balloon member 14, core member 16, and spring tip 18.

Tube 12 is an elongated flexible thin walled metal tube, preferably of stainless steel or of stainless steel with a low friction coating such as polytetrafluoroethylene. Luer fitting 20 is mounted at the proximal end of tube 12 for connection to an inflation device (not shown) which provides fluid under pressure through the interior lumen of tube 12 for balloon inflation.

At its distal end, tube 12 has a section 22 of reduced outside diameter and a formed recess 24 in which the proximal end of core member 16 is attached, preferably by brazing.

Balloon member 14, which is preferably a polymer material such as a polyolefin, has a proximal or waist segment 26, a distensible balloon segment 28, and a small diameter distal segment 30. Proximal segment 26 is bonded to the distal end of tube 12 and to core member 16. An adhesive and sealing material 32 (such as an epoxy) is provided to seal together tube 12 and core member 16 with the proximal segment 26 of balloon member 14.

In the embodiment shown in FIGS. 1 and 2, core member 16 is generally aligned parallel with tube 12 and balloon member 14 and is coaxially aligned except for its proximal end. Core member 16 has a proximal section 34 of larger outer diameter and a distal section 36 of smaller outer diameter. Central vent passage 38 extends essentially the entire length of core member 16, and opens to the exterior of catheter 10 at the proximal end of core member 16. Vent opening 40 provides communication between vent passage 38 and the interior of balloon member 14 to allow for the positive pressure purging of air out through vent opening 40, vent passage 38, and the open proximal end of core member 16.

Distal segment 30 of balloon member 14 is bonded (such as by an epoxy) to the distal end of core segment 36, such as by brazing or soldering. In FIG. 1, core segment 36 extends out slightly beyond the end of distal segment 30, and spring tip 18 is attached to core segment 36. Spring tip 18 includes a solid core segment 42 (which blocks the distal end of vent passage 38), coiled spring 44, and brazed safety button 46. The more proximally located portions of spring 44 are preferably bonded or otherwise attached to the outer end of distal core segment 36.

Distensible segment 28 of balloon member 14 has (by special shaping, wall thickness, or material treatment) a greater tendency to expand under fluid pressure than waist segment 26. The inflation and deflation of balloon member 14, therefore, is primarily confined to distensible segment 28.

In FIG. 1, catheter 10 is shown in a condition in which distensible balloon segment 28 is inflated. Before being inserted into the patient, catheter 10 is connected to an inflation device (not shown) and liquid is supplied under pressure through the interior of tube 12 to the interior of balloon member 14. This liquid purges air contained within the interior of catheter 10 out through vent opening 40 and vent passage 38 to the exterior of catheter 10. Vent opening 40 and passage 38 are sized so that fluid pressure can be supplied to inflate balloon segment 28 without significant leaking of the inflation liquid, and so that air and a small plug of liquid will enter passage 38. When the air has been purged from the interior of catheter 10, the inflation device is then used to draw the liquid back so as to collapse balloon segment 28 around core member 16. This provides a low profile while catheter 10 is being inserted into the patient. The plug of liquid within vent passage 38, however, blocks air from re-entering the interior of balloon segment 28.

The advance of the contrast liquid into passage 38 is controlled by two factors. First, the liquid column is forced through the vent opening 40 by pressure applied to the liquid, and liquid flow is resisted to an extent by the small diameter (about 0.001 to about 0.003 inch) of vent opening 40. Second, once the liquid has entered the passage 38, capillary action which is governed by the surface tension between the liquid and the surface characteristics and diameter of passage 38 will allow the liquid into the core along a certain length until a state of equilibrium is reached. At this point, more pressure would be required to begin movement of the liquid in the column than catheter 10 can be subject to, and therefore the liquid advances no further. This applies to both the application of positive pressure and vacuum. For this reason, catheter 10 is not only ventable through vent opening 40 and passage 38, but is also self-sealing. No additional seal or valve is required to prevent liquid and pressure from bleeding off through this vent passage. The flow characteristics of the radiopaque liquid in the core are dependent on optimization of the capillary action and static breakaway pressure shears.

Catheter 10 is then inserted into the patient and its distal end is advanced through the patient's vascular system to the location of the stenosis which is to be treated. A significant advantage of the present invention is the improved "steerability", "pushability" and "torqueability" (i.e. torque) transfer characteristics which are provided by tube 12. Unlike prior art low profile balloon catheters, in which the main catheter tube or shaft is made of a flexible plastic material, the thin walled metal tube 12 used in catheter 10 of the present invention provides sufficient flexibility to traverse bends, while having improved pushability and improved torque transmitting characteristics.

FIGS. 3 and 4 show dilatation catheter 50, which is another embodiment of the present invention. Catheter 50 includes metal tube 52, balloon member 54, core member 56, spring tip 58 and luer fitting 60.

Tube 52 is an elongated flexible thin walled metal tube of a material such as 304 stainless steel. Tube 52 preferably has a low coefficient of friction coating, such as polytetrafluoroethylene. In one preferred embodiment of the present invention, metal tube 52 has a length of about 43 inches, an inside diameter of about 0.020 inch and an outside diameter of about 0.024 inch.

At the proximal end of metal tube 52 is luer fitting 60. An inflation device (not shown) is connected to fitting 60 for balloon inflation/deflation.

Balloon member 54 is mounted at the distal end of metal tube 52, and is preferably an axially stretchable thermoplastic balloon material which has the ability to have small inside diameter and outside diameter dimensions and a thin wall, while still maintaining an acceptably high burst rating (for example, ten to twelve atmospheres) and a compliance comparable to other balloons used in angioplasty dilatation catheters. Balloon member 54 has a proximal or waist segment 62, a distensible balloon segment 64 and a distal segment 66. Balloon segment 64 is shown in FIG. 3 in its fully inflated condition.

In a preferred embodiment of the present invention, proximal waist segment 62 has a length of about 12 inches, an outside diameter of about 0.034 inch and a wall thickness of about 0.0045 inch. The proximal end of waist segment 62 overlaps and is bonded by epoxy bond 68 to the distal end of metal tube 52 and to a portion of core member 56. Proximal end 70 of waist segment 62 is beveled to provide a smooth profile as catheter 50 is withdrawn from the patient.

As shown in FIG. 3, the wall thickness of balloon segment 64 has a wall thickness which varies from about 0.0045 inch at the end which joins waist segment 62, to a minimum thickness of about 0.001 to about 0.003 inch in central section 64A, (depending on balloon outside diameter) to a wall thickness of about 0.004 inch at the end which joins to distal segment 66. Central segment 64A is about 0.8 inch in length.

Distal segment 66 is bonded by an epoxy bond 72 to spring tip coil 58, which in turn is attached by braze joint 73 to core member 56. The outside diameter of distal segment 66 is about 0.022 inch and the inside diameter is about 0.014 inch. In the bonding region, spring tip coil 58 has an outside diameter of about 0.011 inch to about 0.012 inch, and has a similar or slightly larger outside diameter distal to the bonding region. The diameter of the coil wire forming spring tip coil 58 is about 0.003 inch.

Spring tip coil 58 extends about 0.8 inch beyond the distal segment 66, and is connected to the distal end of core 56 by a braze bond or safety button 74.

The position of the epoxy bond 72 at the same location as braze joint 73 minimizes the length of the relatively stiff region formed by these two joints. Since the objective of catheter 50 is the ability to conform to rather tortuous passages, minimizing the lengths of the stiff region near the distal end of catheter 50 is an advantageous feature of the present invention.

In the embodiment shown in FIG. 3, core member 56 includes vent tube core 76 and solid distal core 78, which are connected together in end-to-end fashion by braze joint and marker 80.

Vent tube core 76 has four sections 76A–76D of differing outside diameters. In a preferred embodiment, segment 76A has an outside diameter of about 0.012 inch, segment 76B has an outside diameter of about 0.009 inch, segment 76C has an outside diameter of about 0.007 inch, and segment 76D has an outside diameter of about 0.006 inch. This transition of decreasing outside diameter in the direction toward the distal end takes advantage of typical curvature of anatomy that catheter 50 will experience in the human body. Preferably, segment 76B has a length of about 4.5 inches and is flexible enough to pass through the aortic arch when the balloon segment 64 is trying to cross the lesion. Segment 76C of vent tube core 76 is preferably about 6 inches in length and is more flexible in order to negotiate the coronary arteries which are typically more tortuous than the aortic arch. Extending through vent tube core 76 is vent passageway 82, which opens to the interior of balloon segment 64 near the proximal end through vent opening 84 and opens to the exterior of catheter 50 through opening 86. Plug 87 blocks the proximal end of vent passage 82 so that pressurized fluid from the interior of metal tube 52 cannot directly enter the proximal end passage 82 and flow out through opening 86.

As shown in FIGS. 3-5, segment 76A of vent tube core 76 is positioned in slot 88 which is formed in the distal end of metal tube 52. In a preferred embodiment, slot 88 is about 0.011 inch wide (which is slightly narrower than the outside diameter of segment 76A) and is about 0.025 inch long. Slot 88 is preferably formed by electrodischarge machining, and segment 76A is brazed in position in slot 88 so that a seal is formed between segment 76A and tube 52.

This preferred bonding of vent tube core 76 to metal tube 52 has the advantage that tube 52 and core 76 maintain good straightness with respect to one other (which is critical for torqueability requirements to prevent whipping of the distal end of catheter 52 as torque is applied to tube 52). In addition, the flow lumen is not as restricted as it would be without the presence of slot 88. In addition, since both the surfaces of vent tube core 76 and metal tube 52 are exposed during processing, the weld can be more reliably made.

It should be noted that the drawings are not drawn to scale. In FIG. 3, for example, the transition of vent core tube 76 from an off-axis connection to tube 52 to a generally coaxial position in more distal portions is much more gradual than shown.

Solid distal core 78 has a segment 78A which has the same outside diameter (0.006 inch) as segment 76D, a segment 78B having an outside diameter of 0.004 inch, and a flat ribbon segment 78C within spring tip 58 which is about 0.001 inch thick and about 0.003 inch wide.

In a preferred embodiment of the present invention, vent tube core 76 and solid distal core 78 are made of the same material, which is preferably a high strength stainless steel or other high strength alloy. 17-7 PH stainless, 18-8 PH stainless or 400 Series heat treatable stainless steel are examples of such high strength materials. The high strength characteristics of vent tube core 76 and solid distal core 78 reduces the chances of them taking on a permanent set when forced through a typical tortuous human anatomy.

In another embodiment of the present invention which is generally similar to the embodiment shown in FIGS. 3-5, except that core member 56 is a single solid core member. In this case, the vent passageway shown in FIG. 3 is not used, and core member 56 can be formed from a single solid wire core and then machined to the desired dimensions.

The advantage of this alternative embodiment of FIG. 5 is that generally a solid wire has somewhat greater strength and hardness than a tube of the same outside diameter. In addition, because core member 56 is an integral member, a bond between two sections of the core member is not required. In order to purge this alternative embodiment catheter, a conventional vacuum purge can be used.

In conclusion, the present invention is an improved angioplasty dilatation balloon catheter of the "non-over-the-wire" type. In other words, it does not require a guide wire which passes through its entire length. With the present invention, a very low profile can be achieved without sacrificing pushability or torque transfer characteristics.

Although the present invention has been described with reference to preferred embodiments, workers skilled in the art will recognize that changes may be made in form and detail without departing from the spirit and scope of the invention.

What is claimed is:

1. A catheter for use in angioplasty, the catheter comprising:

an elongate flexible tubular member having an interior passage extending from a proximal end to a distal end, the tubular member having a longitudinally extending bonding region formed in a portion of a side wall of the tubular member adjacent to its distal end;

a core member having a smaller outer diameter than the tubular member, the core member having a proximal end positioned in the bonding region and bonded to the tubular member and the core member extending distally beyond the distal end of the tubular member;

an inflatable balloon member having a first end bonded to the proximal end of the core member and to the distal end of the tubular member and having a second end connected to the core member, the balloon member extending around the core member and having an interior in fluid communication with the interior passage of the tubular member; and wherein the core member has a vent passage which extends between a vent opening in communication with the interior of the balloon member and an exterior opening proximate the proximal end of the core member.

2. The catheter of claim 1 wherein the balloon member has a proximal waist segment, an intermediate balloon segment, and a distal segment.

3. The catheter of claim 2 wherein the vent opening is positioned near a proximal end of the balloon segment.

4. The catheter of claim 2 wherein the vent opening is positioned near a distal end of the balloon segment.

5. The catheter of claim 1 wherein the core member extends through the second end of the balloon member.

6. The catheter of claim 5 wherein the core member has a spring tip attached at its distal end.

7. The catheter of claim 6 wherein the spring tip has a proximal portion surrounding and bonded to the core member, and wherein the second end of the balloon member surrounds and is bonded to the proximal portion of the spring tip.

8. A catheter for use in angioplasty, the catheter comprising:

an elongate flexible tubular member having an interior passage extending from a proximal end to a distal end, the tubular member having a longitudinally extending bonding region formed in a portion of a side wall of the tubular member adjacent to tis distal end, the bonding region being defined by a longitudinal slot which opens at the distal end of the tubular member;

a core member having a smaller outer diameter than the tubular member, the core member having a proximal end positioned in the bonding region and bonded to the tubular member and the core member extending distally beyond the distal end of the tubular member; and an inflatable balloon member having a first end connected to the distal end of the tubular member and having a second end connected to the core member, the balloon member extending around the core member and having an interior in fluid communication with the interior passage of the tubular member 9. The catheter of claim 8 wherein the longitudinal slot is parallel to a central axis of the tubular member and the balloon member.

10. A balloon catheter comprising:
a catheter shaft formed by a thin-walled tube having a proximal end and a distal end, and having a longitudinally extending bonding region formed in a portion of a side wall of the shaft adjacent to its distal end;
a flexible tube section having a proximal segment connected to the distal end of the shaft, a distal segment, and an inflatable balloon segment therebetween; and
a core extending through the flexible tube section, the core having a distal end portion connected to the distal segment of the flexible tube section and a proximal end portion positioned in the bonding region of the shaft and bonded to the shaft at the bonding region, and with the core having a central vent passage which opens externally of the catheter proximate the proximal portion end of the core, and which opens to an interior of the balloon segment to permit purging of gas from the interior of the balloon segment into the central vent passage.

11. The catheter of claim 10 wherein the distal end of the shaft, the proximal segment of the flexible tube section and the proximal end portion of the core are attached together to form a fluid tight seal.

12. The balloon catheter of claim 10 wherein the core has a vent opening which is positioned near a proximal end of the balloon segment.

13. The balloon catheter of claim 10 wherein the core has a vent opening which si positioned near a distal end of the balloon segment.

14. The balloon catheter of claim 10 wherein the core includes a hollow proximal segment through which the vent passage extends and a solid distal segment joined t the proximal segment.

15. The balloon catheter of claim 10 and further comprising:
a spring tip attached to the distal end portion of the core.

16. The balloon catheter of claim 15 wherein the spring tip has a proximal portion surrounding and bonded to the core, and wherein the distal segment of the flexible tube section surrounds and is bonded to the proximal portion of the spring tip.

17. A balloon catheter comprising:
a catheter shaft formed by a thin-walled tube having a proximal end and a distal end, and having a longitudinally extending bonding region formed in a portion of a side wall of the shaft adjacent to its distal end, the bonding region being defined by a longitudinal slot which opens at the distal end of the shaft;
a flexible tube section having a proximal segment connected to the distal end of the shaft, a distal segment, and an inflatable balloon segment therebetween; and
a core extending through the flexible tube section, the core having a distal end portion connected to the distal segment of the flexible tube section and a proximal end portion positioned in the bonding region of the shaft and bonded to the shaft at the bonding region.

18. A balloon catheter comprising:
a catheter shaft having a proximal end, a distal end, and an inflation lumen extending therethrough; and
an inflatable balloon member connected to the distal end of the catheter shaft with an interior in communication with the inflation lumen; and a core member having a proximal end connected to the distal end of the catheter shaft and a distal end connected to the balloon member, the core member having a vent passage which extends between a vent opening in communication with the interior of the balloon member and an exterior opening which opens to outside the catheter and which is located proximate the proximal end of the core member.

19. The balloon catheter of claim 18 wherein the vent opening is positioned near a proximal end of the balloon member.

20. The balloon catheter of claim 18 herein the vent opening is positioned near a proximal end of the balloon member.

21. The balloon catheter of claim 18 wherein the core member includes a hollow proximal segment through which the vent passage extends and a solid distal segment is joined to the proximal segment.

22. A self-venting balloon catheter comprising:
a catheter shaft having a proximal end, a distal end and an inflation lumen extending therethrough;
an inflatable balloon having a proximal end connected to the distal end of the catheter shaft at a bond therebetween, with an interior of the balloon in communication with the inflation lumen; and
a core member connected to the distal end of the catheter shaft and extending distally through the interior of the balloon member, the core member having a vent passage therein which opens to the interior of the balloon and to an exterior of the catheter for venting air from the interior of the balloon to outside the catheter adjacent the distal end of the catheter shaft but inhibiting escape of liquid from the balloon.

23. The self-venting balloon catheter of claim 22 wherein the core has a distal end bonded to the balloon member.

24. The self-venting balloon catheter of claim 22 wherein the core member has a vent opening which is positioned near the proximal end of the balloon member.

25. The self-venting balloon catheter of claim 22 wherein the core member has a vent opening which is positioned near a distal end of the balloon member.

26. The self-venting balloon catheter of claim 22 wherein the core member includes a hollow proximal segment through which the vent passage extends and a solid distal segment is joined to the proximal segment.

27. A method of making a balloon catheter comprising:
providing a thin-walled tube as a shaft;
forming a longitudinal slot in a portion of a side wall of the tube adjacent a distal end of the tube, with the slot being open at the distal end of the tube;
positioning a proximal end of a core member in the longitudinal slot;
bonding the proximal end of the core member to the tube; and
attaching an inflatable balloon member over the core member so that a proximal segment of the balloon member is connected to the tube and a distal segment of the balloon member is connected to the core member.

28. The method of claim 27 wherein forming the longitudinal slot is by electrodischarge machining.

29. The method of claim 27 and further comprising:
bonding a spring tip to a distal end of the core member.

30. The method of claim 29 wherein bonding a spring tip includes bonding a proximal portion of the spring tip around the core member, and wherein attaching an inflatable balloon includes bonding the distal segment of the balloon around the proximal portion of the spring tip.

31. A catheter for use in angioplasty, the catheter comprising:
an elongated flexible metal tube having a proximal end and a distal end, having a lumen extending therethrough from the proximal end to the distal end, and having a longitudinal slot formed in a side wall adjacent the distal end of the metal tube;
a flexible core member which is shorter than the metal tube, which has a smaller outer diameter than the metal tube, and which has a proximal end positioned in the longitudinal slot and bonded to the metal tube, the core member extending distally beyond the distal end of the metal tube to a distal end; and a flexible tube section which includes a proximal waist segment, an intermediate balloon segment, and a distal segment, the proximal waist segment being connected at its proximal end to the distal end of the metal tube and the distal segment being connected to the core member; the core member extending through the proximal waist segment, through the intermediate balloon segment and out the distal end of the distal segment; and an interior of the inflatable balloon segment being in fluid communication with the lumen of the metal tube.

* * * * *

UNITED STATES PATENT AND TRADEMARK OFFICE
CERTIFICATE OF CORRECTION

PATENT NO. : 4,943,278
DATED : July 24, 1990
INVENTOR(S) : Charles L. Euteneuer et al.

It is certified that error appears in the above-identified patent and that said Letters Patent is hereby corrected as shown below:

Col. 7, line 5, delete "tis", insert --its--

Col. 7, line 20-21, delete "member", insert --member.--

Col. 7, line 54, delete "si", insert --is--

Col. 7, line 58, delete "t", insert --to--

Col. 8, line 36, delete "herein", insert --wherein--

Col. 8, line 37, delete "proximal", insert --distal--

Signed and Sealed this

First Day of October, 1991

Attest:

Attesting Officer

HARRY F. MANBECK, JR.

Commissioner of Patents and Trademarks